(12) United States Patent
Rao et al.

(10) Patent No.: US 8,288,514 B2
(45) Date of Patent: Oct. 16, 2012

(54) METHOD OF PREPARING CLARITHROMYCIN

(75) Inventors: Xintang Rao, Yiwu (CN); Zhijian Ding, Yiwu (CN); Hangbin Lou, Yiwu (CN); Jing Wu, Yiwu (CN); Yanglin Fang, Yiwu (CN); Baineng Deng, Yiwu (CN)

(73) Assignee: Zhejiang Huayi Pharmaceutical Co., Ltd., Yiwu, Zhejiang Province (CN)

( * ) Notice: Subject to any disclaimer, the term of this patent is extended or adjusted under 35 U.S.C. 154(b) by 167 days.

(21) Appl. No.: 12/770,869

(22) Filed: Apr. 30, 2010

(65) Prior Publication Data

US 2010/0280230 A1 Nov. 4, 2010

(30) Foreign Application Priority Data

Apr. 30, 2009 (CN) .......................... 2009 1 0098150

(51) Int. Cl.
*C07H 17/08* (2006.01)

(52) U.S. Cl. ....................................... 536/7.2; 536/18.5

(58) Field of Classification Search ................... 536/7.2, 536/7.3, 7.4
See application file for complete search history.

(56) References Cited

U.S. PATENT DOCUMENTS 4,331,803 A 5/1982 Watanabe et al.

FOREIGN PATENT DOCUMENTS

EP 0272110 6/1988

OTHER PUBLICATIONS

Gasc et al., New Ether Oxime Derivatives of Erythromycin A: A Structure-Activity Relationship Study, J. of Antibiotics, 1991, vol. 44 No. 3, 313-330.

*Primary Examiner* — Elli Peselev
(74) *Attorney, Agent, or Firm* — Jacobson Holman PLLC

(57) ABSTRACT

This invention discloses a method of manufacturing clarithromycin, where an erythromycin A 9-oxime thiocyanate salt is used directly to perform an etherification reaction, and then successively silanizattion, methylattion and hydrolysis reactions are sequentially conducted. It is a new process with simple process with a high yield, low cost, less pollution, high quality and is suitable for commercial manufacturing.

5 Claims, No Drawings

METHOD OF PREPARING CLARITHROMYCIN

The present application claims the priority benefit of Chinese Patent Application No. 200910098150.X, filed on Apr. 30, 2009, which is hereby incorporated by reference in its entirety.

FIELD OF TECHNOLOGY

The present invention relates to the technical field of preparing an organic compound, specifically a method of preparing clarithromycin.

BACKGROUND

Clarithromycin (structural formula I), also known as methyl-erythromycin, is a macrolide antibiotic obtained from methylation of 6-position hydroxyl group of erythromycin. It exhibits excellent anti-bacterial activity against Gram-positive bacteria, some Gram-negative bacteria, anaerobic bacteria, mycoplasma and chlamydia. Its activity is 2-4 times stronger than erythromycin. However, its toxicity is only about half ($\frac{1}{2}$) to one twentyfourth ($\frac{1}{24}$) of the toxicity of erythromycin.

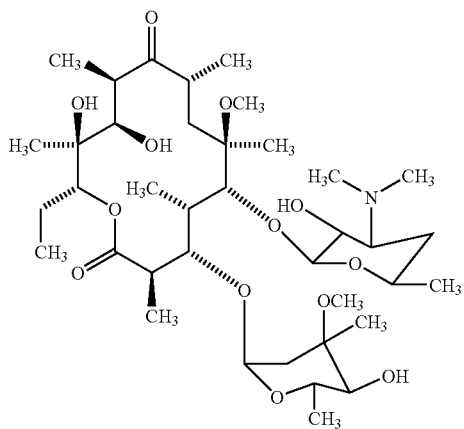

(I)

U.S. Pat. No. 4,331,803 discloses a method of making clarithromycin by protecting the hydroxyl group at 2'-position and the dimethylamine group at 3'-position of erythromycin A, conducting methylation of 6-position hydroxyl group of erythromycin A, and removing the protective groups from erythromycin. Because the hydroxyl group at the 11, 12, and 4' positions of erythromycin A can be easily methylated in a methylation reaction, many by-products are produced. It makes purification of the product difficult and affects the quality and the yield of the product.

In order to effectively methylate hydroxyl groups at the 6-positions, EP0272110 discloses a method of preparing clarithromycin. First, erythromycin A 9-oxime is etherified with an acid catalysis to protect the hydroxyl group at the 9-position. Next, the hydroxyl groups at the 2'-position and 4"-position are silylanized to be protected. Then, the hydroxymethylation reaction is conducted at the 6-positions. Finally, hydrolyzation is conducted to remove the protecting groups at the 2'-position, the 4"-position and the 9-position to obtain clarithromycin. This technological route is long and the yield is not high. Morever, because macrolide antibiotic is not stable to acid, when an acid catalysis is used to protect the hydroxyl group at the 9-position, erythromycin A 9-oxime is easily destroyed, thereby the yield is reduced. The total yield is about 50% (according to erythromycin A 9-oxime).

SUMMARY OF THE INVENTION

An object of the present invention is to provide a synthesis method of clarithromycin which has a simple process, a high yield, low cost, less pollution, high quality and is suitable for the commercial manufacturing. To solve the technical problems mentioned above, the present invention adopts the following technical solution:

Erythromycin A 9-oxime thiocyanate salt (formula II) is etherified directly, then sequentially goes through the silanization, methylation and hydrolysis reactions. The reaction route is as follows:

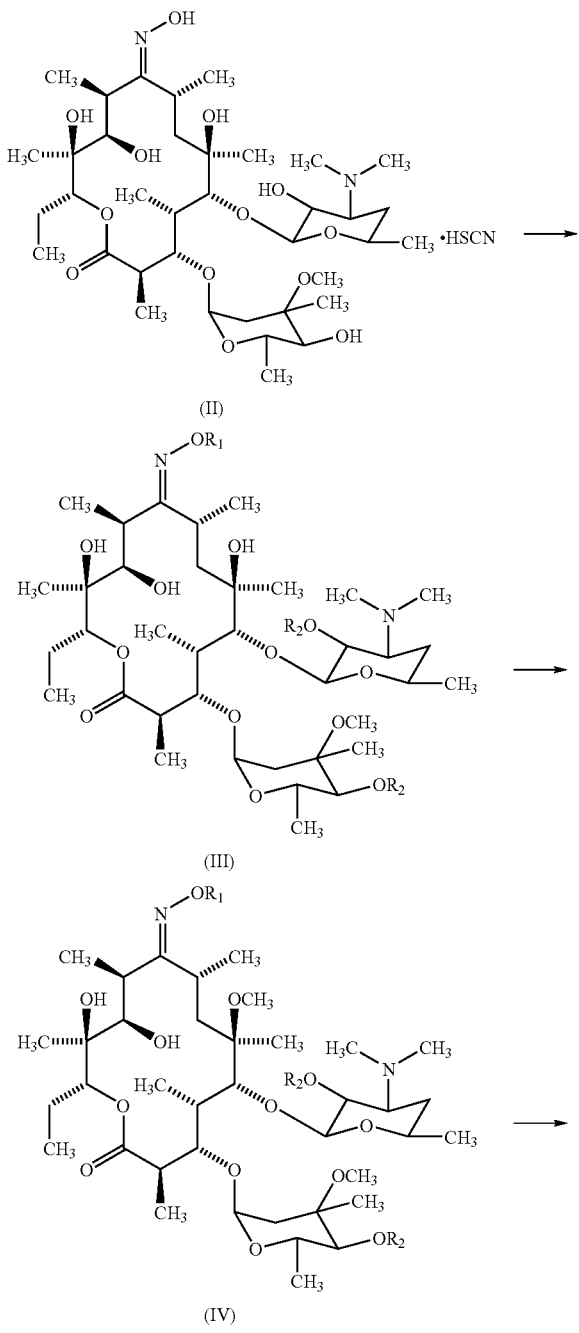

(I)

wherein: $R_1$ is the protective group of the etherification reaction and $R_1$ can be 1-ethoxy-1-methylethyl, 1-methoxyl-1-methylethyl, 2-ethoxypropyl or 1-ethoxycyclohexyl, etc.; $R_2$ is trimethylchlorosilane.

The present invention comprises the following steps:

1. Erythromycin A 9-oxime thiocyanate salt is dissolved in an organic solvent. An etherifying agent is added until the reaction completes. Then, a silanizing agent is added into the reaction and erythromycin A 9-oxime silanization derivatives (III) are obtained. The organic solvent herein can be haloalkanes, dimethyl sulfoxide, dimethylformamide, methylbenzene, C6 to C10 lower paraffin hydrocarbon, ethyl acetate, acetone, etc., preferably dichloromethane. The etherifying agent can be 2-ethoxypropene, 2-methoxypropene, 2,2-dimethoxypropane, 1,1-dimethoxy-Cyclohexane, preferably 2-ethoxypropene. The temperature of the etherification can be −20° C. to 80° C., preferably the room temperature. The dosage of the etherifying agent is equivalent to 1-20 times of erythromycin A 9-oxime thiocyanate salt, preferably 6 times. The silanizing agent can be trimethylchlorosilane, hexamethyldisilazane, preferably trimethylchlorosilane. The dosage of the silanizing agent is equivalent to 1-2 times of erythromycin A 9-oxime thiocyanate salt. The temperature of the silanization can be −10° C. to 50° C., preferably the room temperature.

2. The next step is to methylate the silanization derivatives from the previous step. After the reaction completes, water is added to obtain methide (IV). The methylating agent can be halomethane, the dosage of which is equivalent to 1-5 times of silanization derivatives. The alkali can be selected from sodium hydroxide and potassium hydroxide, the dosage of which is equivalent to 1-5 times of silanization derivatives. The methylation solvent can adopt the mixture of dimethyl sulfoxide and tetrahydrofuran. The reaction temperature is −10 to 30° C.

3. Hydrolysis reaction of the methide from the last step removes the protective groups and obtain clarithromycin (I). Ethanol can be the solvent of the hydrolysis reaction. Formic acid and sodium bisulfite can be used as a reductant in a reflux reaction.

Erythromycin A 9-oxime thiocyanate salt used as the starting material of the present invention can be prepared in an usual processes (such as J. Antibio.1991,44(3), 313-330).

Comparing the prior technology adopting erythromycin A 9-oxime in the etherification, the present invention uses erythromycin A 9-oxime thiocyanate salt to achieve the etherification. The present invention has following advantages:

1. The present invention leaves out a reaction step of the transformation from erythromycin A 9-oxime thiocyanate salt to erythromycin A 9-oxime, which simplifies the production process. In addition, there is no need to conduct the unit operations, such as neutralization reaction of alkali, extraction, water-washing, centrifugal and drying and so on.

2. In the present invention, reducing the reaction step saves the materials required for the step (usually dichloromethane, ammonia and methanol), thereby the cost of final product clarithromycin can be reduced.

3. Because of reducing the one reaction step and centrifugal process, the exhaust and the pollution are decreased.

4. There is no need to add acid catalyst in the etherification. Therefore, the etherification reaction is stable and the acidity destruction is avoided.

5. The present invention uses erythromycin A 9-oxime thiocyanate as the raw material to operate etherification directly, then sequentially performs silicon alkylation, methylation and hydrolysis reactions to obtain clarithromycin. Compared with the method of using erythromycin A 9-oxime as the raw material, the yield of the present invention is higher. The total yield is above 60% (accounting in erythromycin A 9-oxime thiocyanate salt), and the product quality of the present invention is better.

EMBODIMENTS OF THE INVENTION

The following embodiments help to further comprehend the present invention. However, the contents of the invention are not limited to these embodiments.

Example 1

Preparation of erythromycin A 9-oxime thiocyanate salt 200 g of methanol, 200 g of erythromycin thiocyanate, 100 g of hydroxylamine hydrochloride, and 60 g of triethylamine were added into a 1000 ml 4-neck flask with a stirring paddle. The mixture in the flask was heated up until circumfluence, and kept warm for 24 hours. Then its temperature was dropped to 0° C. It was filtered and dried to obtain 176 g of erythromycin A 9-oxime thiocyanate salt. The yield was 86.2%.

Example 2

Preparation of 2',4"-O-Bis (trimethylsilyl)erythromycin A9-[O-(1-ethoxy-1-methylethyloxime)]

100 g of dichloromethane and 30 g of erythromycin A 9-oxime thiocyanate salt were added into a 500 ml reaction bulb. 20 g of 2-Ethoxypropene was added dropwise at the normal temperature during 20 minutes. After the mixture was kept warm for 10 minutes, 15 g of imidazole, 15 g of trimethylchlorosilane were added dropwisely at the normal temperature during 30 minutes. After the mixture was kept warm for 10 minutes, 50 ml of water was added. The mixture went through delamination and the aqueous layer was removed. The dichloromethane layer was washed twice with water (50 ml ×2). The dichloromethane layer was concentrated to dry. 100 g of methanol was added. The mixture was filtered and dried to obtain 37 g of 2',4"-O-Bis(trimethylsilyl)erythromycin A 9-[O-(1-ethoxy-1-methylethyloxime)] (erythromycin A 9-oxime silanization derivatives). The yield is 94.1%.

Example 3

Preparation of 2',4"-O-Bis(trimethylsilyl)-6-O-methylerythromycin A 9-[O-(1-ethoxy-1-methylethyloxime)]

35 g of erythromycin A 9-oxime silanization derivatives and 150 g of tetrahydrofuran were added into a 500 ml reaction bulb. After complete dissolution, 165 g dimethyl sulfoxide, 13.5 g of iodomethane and 8.5 g of KOH were added. The mixture was kept warm at the room temperature for 60 minutes. 100 ml of water was added. The mixture was filtered to obtain 35.5 g 2',4"-O-Bis(trimethylsilyl)-6-O-methylerythromycin A 9-[O-(1-ethoxy-1-methylethyloxime)](methide). The yield is 100%.

Example 4

Preparation of clarithromycin 35 g of methide obtained in Example 3, 112 g of ethanol, 10 g of formic acid, 30 g of sodium bisulfite and 100 g of water were added into a 500 ml reaction bulb. The mixture was heated up until circumfluence. After the reaction lasted for 8 hours, the temperature was dropped to the normal temperature. 250 g of dichloromethane was added for extraction and delaminating the mixture. The dichloromethane layer was concentrated to dry and 17.5 g clarithromycin was obtained. The yield is 66.7%.

The invention claimed is:
1. A method of preparing clarithromycin of formula (I)

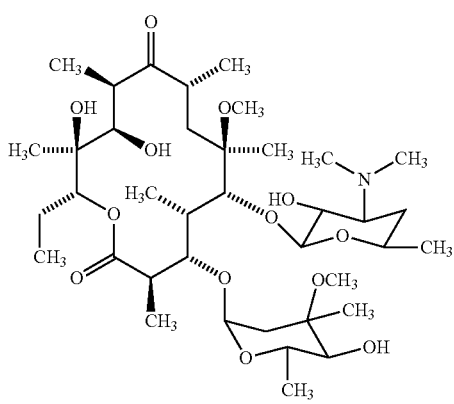

(I)

comprising the steps of:
providing erythromycin A 9-oxime thiocyanate of formula (II):

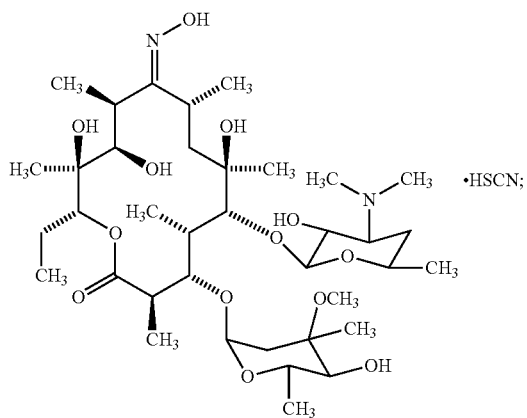

(II)

conducting an etherification reaction by dissolving erythromycin A 9-oxime thiocyanate in an organic solvent to form a solution and adding an etherifying agent into the solution;
conducting a silicon alkylation reaction by adding a silanizing agent into product of the etherification reaction to obtain erythromycin A 9-oxime silanization derivatives of formula (III)

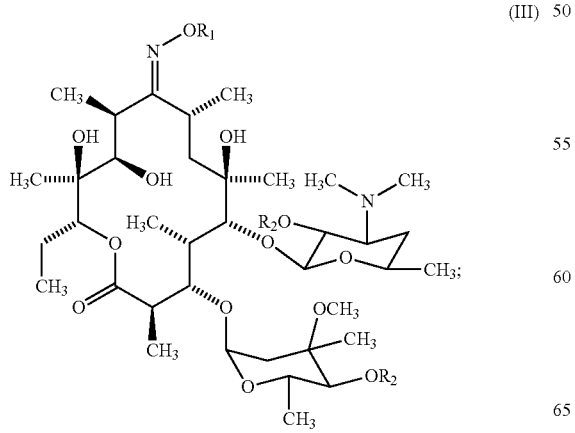

(III)

conducting a methylation reaction by adding a methylating agent into product of the silicon alkylation reaction to obtain methide of formula (IV)

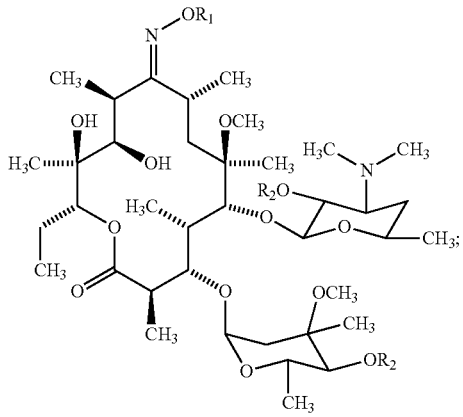

(IV)

conducting a hydrolysis reaction to obtain clarithromycin of formula (I);
wherein $R_1$ is 1-ethoxy-1-methylethyl, 1-methoxyl-1-methylethyl, 2-ethoxypropyl or 1-ethoxycyclohexyl; and $R_2$ is trimethylchlorosilane.

2. The method of claim 1, wherein the organic solvent adopted in the etherification reaction is selected from haloalkanes, dimethyl sulfoxide, dimethylformamide, methylbenzene, and C6 to C10 lower paraffin hydrocarbon.

3. The method of claim 1, wherein the etherifying agent used in the etherification reaction is selected from 2-Ethoxypropene, 2-Methoxypropene, 2,2-Diethoxypropane, and 1,1-diethoxy-Cyclohexane.

4. The method of claim 1, wherein the reaction temperature of the etherification reaction is between −20° C. to 80° C.

5. A method of preparing clarithromycin comprising the steps of:
(i) preparing erythromycin A 9-oxime thiocyanate salt by mixing methanol, erythromycin thiocyanate, hydroxylamine hydrochloride, and triethylamine, heating the mixture until circumfluence, keeping the mixture warm for 24 hours, dropping the temperature to 0° C., filling the mixture to obtain erythromycin A 9-oxime thiocyanate salt;
(ii) preparing 2',4"-O-Bis (trimethylsilyl)erythromycin A9-[O-(1-ethoxy-1-methylethyloxime)] by mixing dichloromethane and erythromycin A 9-oxime thiocyanate salt, adding 2-Ethoxypropene dropwise at room temperature, adding imidazole and trimethylchlorosilane dropwise at room temperature, and filtering and drying the mixture to obtain 2',4"-O-Bis(trimethylsilyl) erythromycin A 9-[O-(1-ethoxy-1-methylethyloxime)];
(iii) preparing 2',4"-O-Bis(trimethylsilyl)-6-O-methylerythromycin A 9-[O-(1-ethoxy-1-methylethyloxime)] by mixing 2',4"-O-Bis(trimethylsilyl)erythromycin A 9-[O-(1-ethoxy-1-methylethyloxime)] and tetrahydrofuran, adding dimethyl sulfoxide, iodomethane and KOH to the mixture, filtering and drying the mixture to obtain 35.5 g 2',4"-O-Bis(trimethylsilyl)-6-O-methylerythromycin A 9-[O-(1-ethoxy-1-methylethyloxime)] (methide); and
(iv) preparing clarithromycin by mixing methide, ethanol, formic acid, sodium bisulfite and water, heating the mixture until circumfluence, reducing the temperature to room temperature, adding dichloromethane and delaminating the mixture, and concentrating and drying dichloromethane layer to obtain clarithromycin.

* * * * *